(12) United States Patent
Gono

(10) Patent No.: US 9,345,385 B2
(45) Date of Patent: May 24, 2016

(54) SUBJECT OBSERVATION APPARATUS AND SUBJECT OBSERVATION METHOD

(75) Inventor: Kazuhiro Gono, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 1981 days.

(21) Appl. No.: 12/505,751

(22) Filed: Jul. 20, 2009

(65) Prior Publication Data

US 2010/0022858 A1    Jan. 28, 2010

(30) Foreign Application Priority Data

Jul. 23, 2008   (JP) .................. 2008-190175
Jul. 23, 2008   (JP) .................. 2008-190176

(51) Int. Cl.

| A61B 1/00 | (2006.01) |
|---|---|
| A61B 1/04 | (2006.01) |
| A61B 1/045 | (2006.01) |
| A61B 5/00 | (2006.01) |
| G01N 21/47 | (2006.01) |
| G02B 23/24 | (2006.01) |

(52) U.S. Cl.
CPC ............ *A61B 1/00096* (2013.01); *A61B 1/041* (2013.01); *A61B 1/045* (2013.01); *A61B 5/0084* (2013.01); *G01N 21/474* (2013.01); *G01N 21/4788* (2013.01); *G01N 2021/4711* (2013.01); *G01N 2021/4716* (2013.01); *G02B 23/2407* (2013.01)

(58) Field of Classification Search
CPC .... A61B 1/00096; A61B 1/041; A61B 1/045; A61B 5/0084; G01N 21/474; G01N 21/4788; G01N 2021/4711; G01N 2021/4716; G02B 23/2407

See application file for complete search history.

(56) References Cited

U.S. PATENT DOCUMENTS

| 5,028,135 A | 7/1991 | Cheung |
|---|---|---|
| 5,305,073 A | 4/1994 | Ford, Jr. |
| 6,420,709 B1 | 7/2002 | Block et al. |
| 6,690,520 B1 | 2/2004 | Kusuzawa |
| 2004/0246477 A1* | 12/2004 | Moon et al. .................. 356/300 |
| 2005/0213092 A1* | 9/2005 | MacKinnon et al. .......... 356/336 |

(Continued)

FOREIGN PATENT DOCUMENTS

| EP | 1 787 577 A1 | 5/2007 | |
|---|---|---|---|
| JP | 61169819 A * | 7/1986 | ................ G02F 1/03 |

(Continued)

OTHER PUBLICATIONS

Anderson et al., "Microscope imaging through highly scattering media", Optics Letters, OSA, Optical Society of America, vol. 19, No. 13, Jul. 1, 1994, pp. 981-983, XP000454703.

(Continued)

*Primary Examiner* — Bo J Peng
(74) *Attorney, Agent, or Firm* — Scully, Scott, Murphy & Presser, P.C.

(57) ABSTRACT

A subject observation apparatus of the invention includes: a light-emitting section for emitting a light to a subject; an optical modulation section for detecting a scattering angle of a return light from the subject and performing optical modulation on the return light in accordance with the scattering angle; and a signal output section for generating a signal to show a state of light scattering in the subject based on the light subjected to the optical modulation by the optical modulation section, and outputting the generated signal.

5 Claims, 10 Drawing Sheets

(56) References Cited

U.S. PATENT DOCUMENTS

2007/0070260 A1* 3/2007 Wang .................. 349/18
2007/0133002 A1 6/2007 Wax et al.
2007/0263226 A1* 11/2007 Kurtz et al. .................. 356/492

FOREIGN PATENT DOCUMENTS

| JP | 62-044650 A | 2/1987 |
| JP | 03-013847 A | 1/1991 |
| JP | 06-043090 A | 2/1994 |
| JP | 09-304723 A | 11/1997 |
| JP | 10-221248 A | 8/1998 |
| JP | 10-246697 A | 9/1998 |
| JP | 11-173969 A | 7/1999 |
| JP | 11-258167 | 9/1999 |
| JP | 2000-230901 A | 8/2000 |
| JP | 2001-519190 A | 10/2001 |
| JP | 2002-535645 A | 10/2002 |
| JP | 2005-040175 A | 2/2005 |
| JP | 2006-341078 | 12/2006 |
| JP | 2007-325781 | 12/2007 |
| WO | WO 2007000574 A1 * | 1/2007 ............. G01N 15/14 |
| WO | WO 2007/133684 A2 | 11/2007 |
| WO | WO 2008/011056 A2 | 1/2008 |

OTHER PUBLICATIONS

Japanese Office Action dated Oct. 23, 2012 in corresponding Japanese Patent Application No. 2008-190175.

Japanese Office Action dated Nov. 13, 2012 in Japanese Patent Application No. 2008-190176.

Japanese Office Action dated Sep. 10, 2013 issued in Japanese Patent Application No. JP 2008-190176.

Japanese Office Action dated Jul. 1, 2014 issued in Japanese Patent Application No. JP 2008-190176.

* cited by examiner

SUBJECT OBSERVATION APPARATUS AND SUBJECT OBSERVATION METHOD

This application claims benefit of Japanese Applications No. 2008-190175 filed in Japan on Jul. 23, 2008 and No. 2008-190176 filed in Japan on Jul. 23, 2008, the contents of which are incorporated by this reference.

BACKGROUND OF THE INVENTION

1. Field of the Invention

The present invention relates to a subject observation apparatus and a subject observation method, and more particularly to a subject observation apparatus and a subject observation method for observing a subject based on a modulated light obtained by modulating a scattered light from the subject.

2. Description of the Related Art

Techniques have been conventionally proposed for detecting a scattering angle distribution of a return light from a subject and observing a state of the subject based on the scattering angle distribution. For example, Japanese Patent Application Laid-Open Publication No. 11-258167 discloses a technique for a method of inspecting a defection in a glass tube. In the technique, a laser light is almost vertically irradiated onto an outer surface or an inner surface of a glass tube to detect intensity and angle distribution of a scattering light caused by the laser light reflected from the glass tube, and based on the detected intensity and angle distribution of the scattering light, the defection size of the glass tube is determined and a bubble streak is discriminated from an extraneous substance.

Meanwhile, techniques have been conventionally proposed for observing a state of capillary vessels in the vicinity of a mucosa surface layer. For example, Japanese Patent Application Laid-Open Publication No. 2006-341078 discloses a biological observation apparatus having a configuration for generating a narrowband spectral image in which structure of capillary vessels of a mucosa surface layer is highlighted.

SUMMARY OF THE INVENTION

A subject observation apparatus according to the present invention includes: a light-emitting section for emitting a light to a subject; an optical modulation section for detecting a scattering angle of a return light from the subject and performing optical modulation on the return light in accordance with the scattering angle; and a signal output section for generating a signal to show a state of light scattering in the subject based on the light subjected to the optical modulation by the optical modulation section, and outputting the generated signal.

A subject observation apparatus according to the present invention includes: a light-emitting section for emitting a light to a subject; an optical modulation section for detecting a scattering angle of a return light from the subject and performing optical modulation on the return light in accordance with the scattering angle; and an image pickup device for picking up an image of the subject based on the light subjected to the optical modulation by the optical modulation section.

A subject observation method according to the present invention includes: emitting a light to a subject; detecting a scattering angle of a return light from the subject and performing optical modulation on the return light in accordance with the scattering angle; and generating a signal to show a state of light scattering in the subject based on the light subjected to the optical modulation, and outputting the generated signal.

A subject observation method according to the present invention includes: emitting a light to a subject; detecting a scattering angle of a return light from the subject and performing optical modulation on the return light in accordance with the scattering angle; and picking up an image of the subject based on the light subjected to the optical modulation.

DETAILED DESCRIPTION OF THE PREFERRED EMBODIMENTS

Hereinafter, embodiments of the present invention will be described with reference to the drawings.

Figure 1:
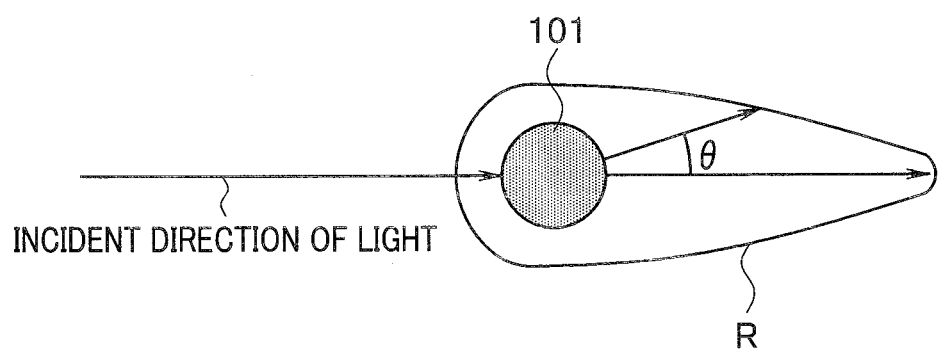
FIG. 1 is a view schematically showing a scattering characteristic when a light is incident on a scattering object.
Figure 2:
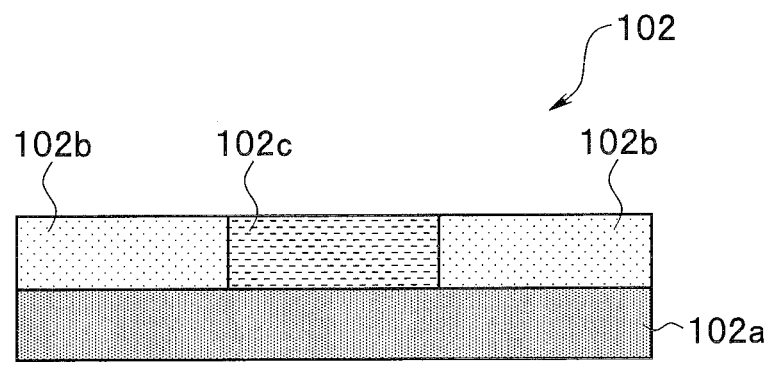
FIG. 2 is a view showing an example of a subject including a plurality of regions each having a different scattering characteristic.
Figure 3:
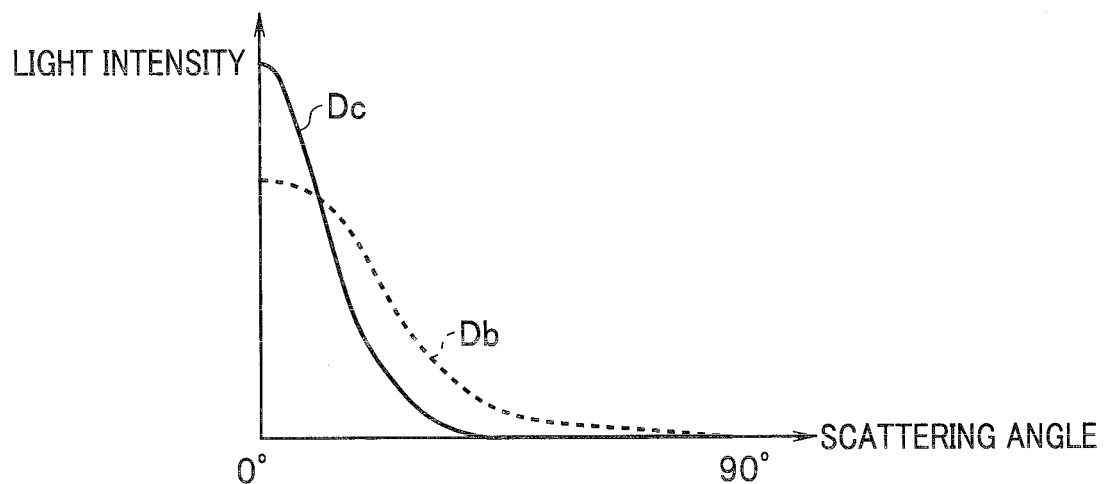
FIG. 3 is a view showing intensity distributions of scattering lights corresponding to scattering angles in two different scattering media.

First, description will be made on principles used in the embodiments of the present invention. FIG. 1 is a view schematically showing a scattering characteristic when a light is incident on a scattering object. FIG. 2 is a view showing an example of a subject including a plurality of regions each having a different scattering characteristic. FIG. 3 is a view showing intensity distributions of scattering lights corresponding to scattering angles in two different scattering media.

As shown in FIG. 1, when forward-scattering occurs by a light incident horizontally from the left side of the paper surface of the drawing onto a scattering object 101, the light is scattered with the scattering characteristic schematically shown as a closed curve R, for example.

When the angle in the forward direction with respect to the advancing direction of the light incident on the scattering object 101 is assumed to be 0 degree and the angle in the opposite direction with respect to the advancing direction of the light incident on the scattering object 101 is assumed to be 180 degrees, a scattering angle $\theta$ is defined as a value which is expressed as $0° \leq \theta \leq 180°$ Now, description will be made by taking as an example a subject 102 including a two-layer structure made up of an upper layer and a lower layer as shown in FIG. 2.

An absorbing object 102a, which exhibits a strong light-absorption characteristic, uniformly exists in the lower layer of the subject 102.

On the other hand, the upper layer of the subject 102 has a structure divided into three regions, that is, left, right, and central regions. In the three regions, a first scattering medium 102b, which exhibits a relatively weak forward-scattering characteristic, exists in the left and right regions, and a second scattering medium 102c, which exhibits a relatively strong forward-scattering characteristic, exists in the central region.

When a light is incident vertically and uniformly on the subject 102 having the above-described structure from the upper side of the paper surface of the drawing, the distribution of the scattering angle $\theta$ corresponding to the intensity of the scattering light (return light) from the scattering medium 102b is as shown by the curve Db in FIG. 3. In addition, when a light is incident vertically and uniformly on the subject 102 having the above-described structure from the upper side of the paper surface of the drawing, the distribution of the scattering angle $\theta$ corresponding to the intensity of the scattering light (return light) from the scattering medium 102c is as shown by the curve Dc in FIG. 3.

Note that the intensity distributions of the scattering lights (return lights) corresponding to the scattering angle $\theta$, which are shown as the curves Db and DC in FIG. 3, are perceived based on the following inference.

When it is assumed that the subject 102 is a living tissue, for example, a large part of the light incident on the subject 102 is multiply-scattered inside the living tissue. In this case, in view of the fact that the light to be incident on an objective optical system of the image pickup apparatus is a resultant light of the multiple scattering inside the living tissue, observation is performed assuming that the light is emitted by strong forward-scattering from the scattering object located immediately below the surface of the living tissue. That is, observation performed on the light multiply-scattered by the living tissue is equivalent to the observation performed on the forward-scattering light emitted from the scattering object located immediately below the surface of the living tissue.

According to the above-described inference, as shown in FIG. 3, each of the first scattering medium 102b and the second scattering medium 102c has a different forward-scattering characteristic, so that the distributions of the scattering angle $\theta$ corresponding to the intensity of the scattering light (return light) are different from each other.

Next, description will be made on a configuration and working of the subject observation apparatus, which uses the above-described principle, according to the embodiments of the present invention.

First Embodiment

Figure 4:
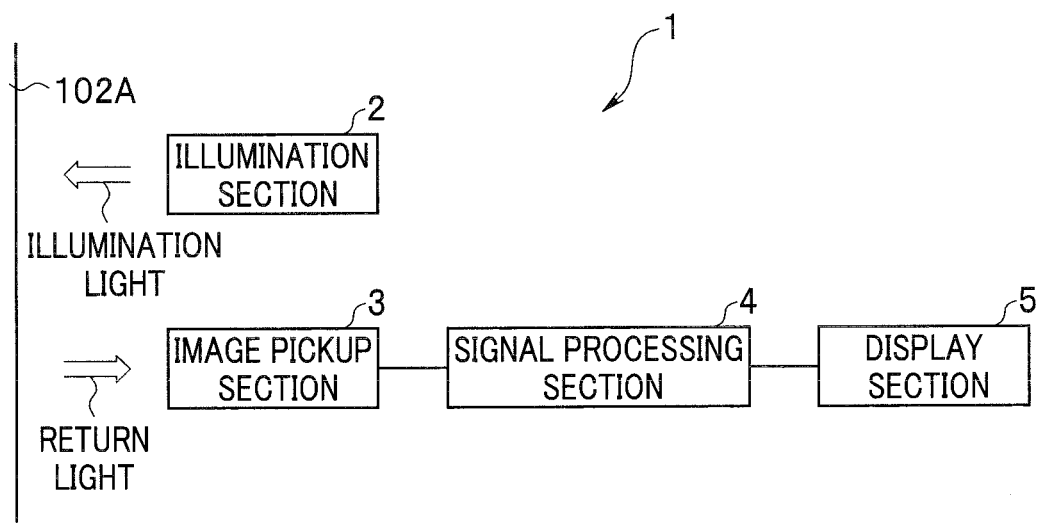
FIG. 4 is a view showing a configuration of a main part of a subject observation apparatus according to a first embodiment of the present invention.
Figure 5:
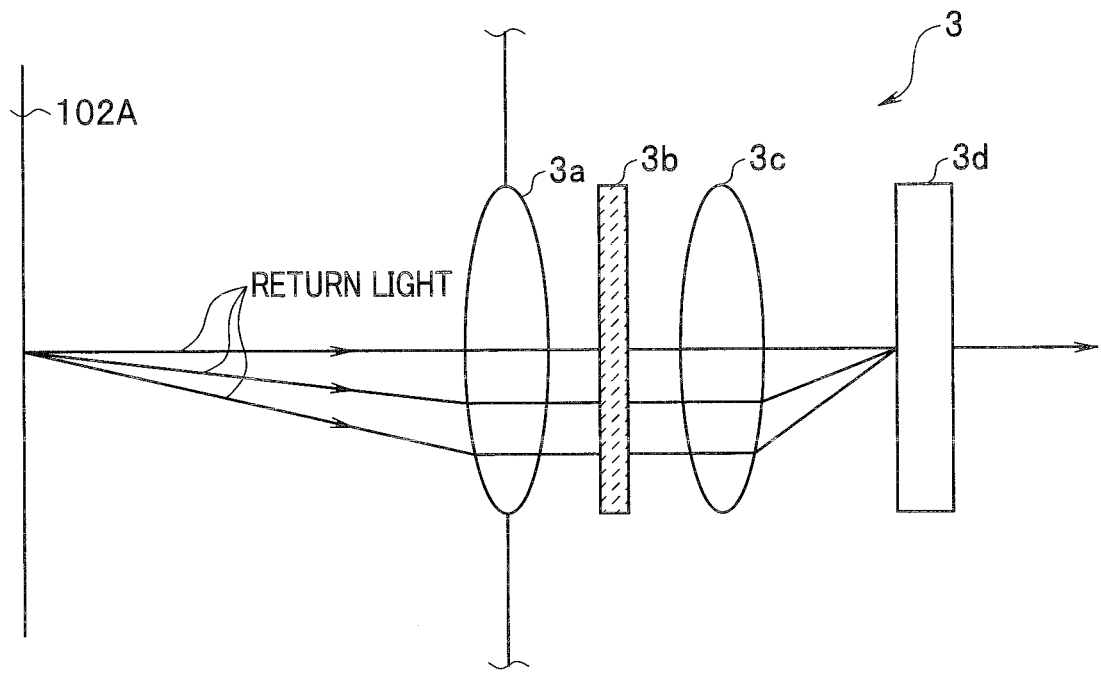
FIG. 5 is a view showing an example of a specific configuration of an image pickup section included in the subject observation apparatus according to the first embodiment of the present invention.
Figure 6:
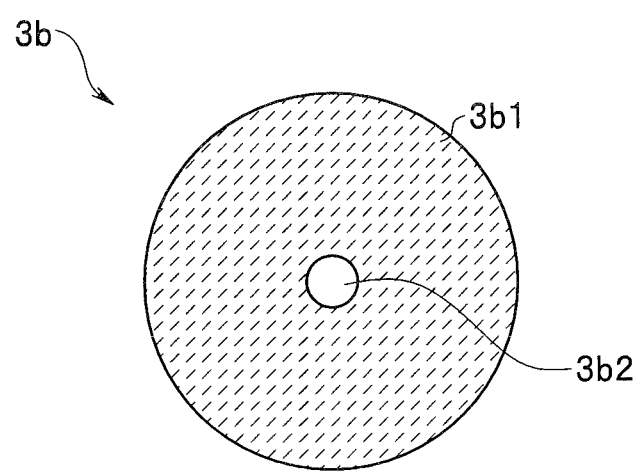
FIG. 6 is a view showing an example of a specific configuration of an optical modulator included in the image pickup section in FIG. 5.
Figure 7:
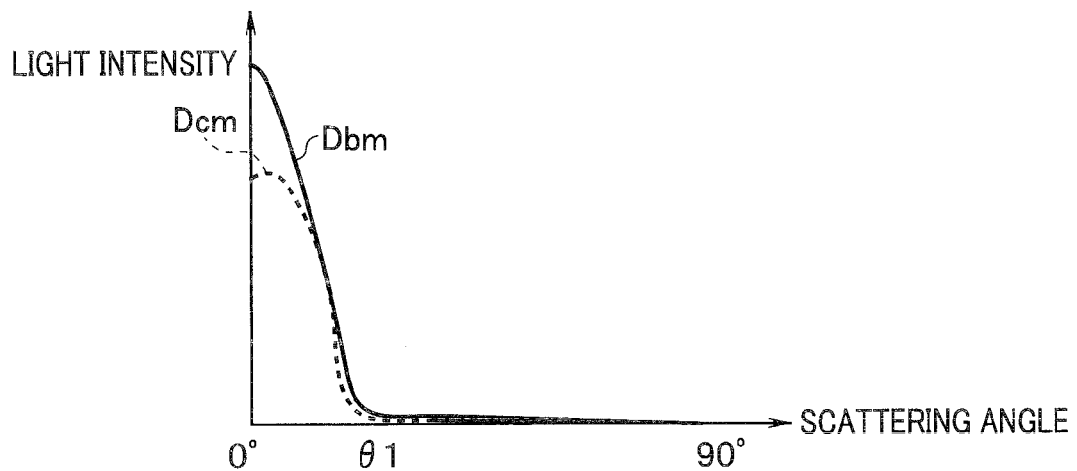
FIG. 7 is a view showing a modulation result in a case where optical modulation has been performed by the optical modulator in FIG. 6 on the scattering lights having the scattering angle distributions in FIG. 3.
Figure 8:
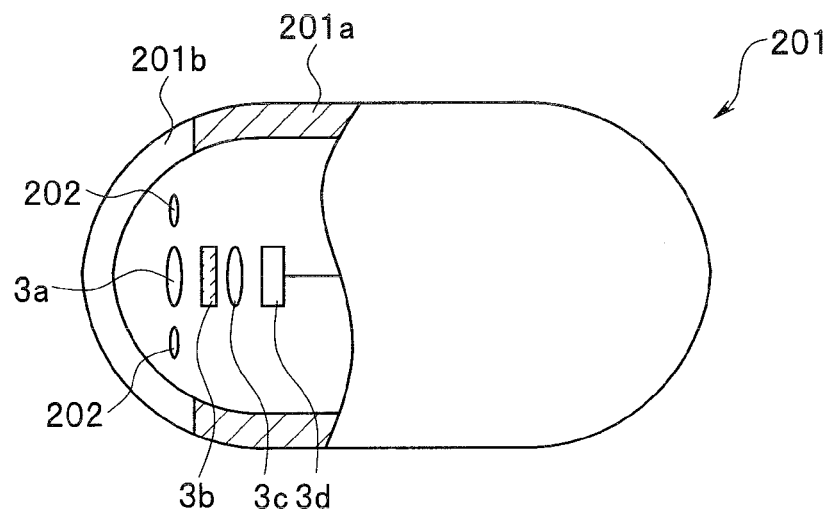
FIG. 8 is a view showing an example in a case where a part of the configuration of the subject observation apparatus according to the first embodiment of the present invention is applied to a capsule medical apparatus.
Figure 9:
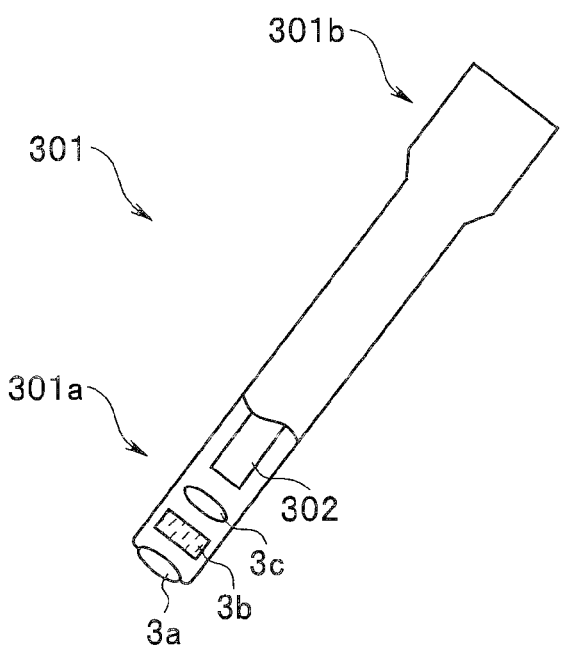
FIG. 9 is a view showing an example in a case where a part of the configuration of the subject observation apparatus according to the first embodiment of the present invention is applied to a rigid endoscope.
Figure 10:
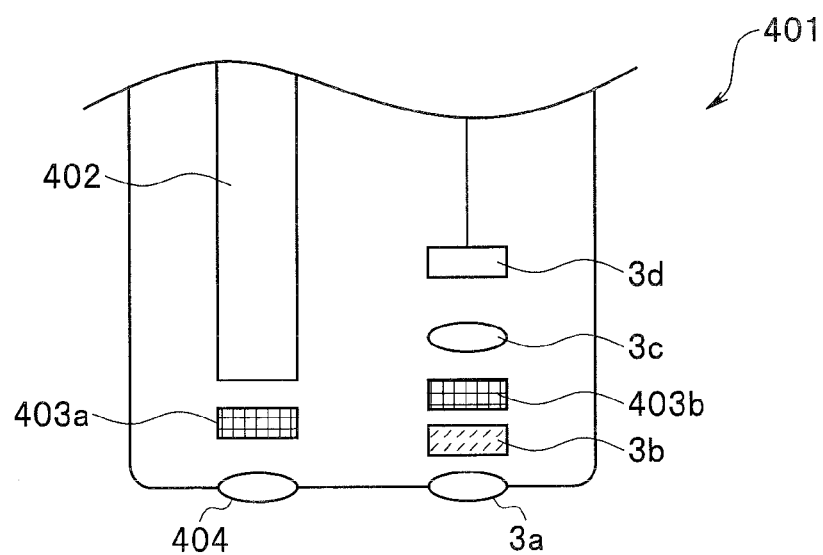
FIG. 10 is a view showing an example in a case where a part of the configuration of the subject observation apparatus according to the first embodiment of the present invention is combined with a configuration for polarized imaging.

FIGS. 4 to 13 relate to the first embodiment of the present invention. FIG. 4 is a view showing a configuration of a main part of the subject observation apparatus according to the first embodiment of the present invention. FIG. 5 is a view showing an example of a specific configuration of an image pickup section included in the subject observation apparatus according to the first embodiment of the present invention. FIG. 6 is a view showing an example of a specific configuration of an optical modulator included in the image pickup section in FIG. 5. FIG. 7 is a view showing a modulation result in a case where optical modulation has been performed by the optical modulator in FIG. 6 on the scattering lights having the scattering angle distributions in FIG. 3. FIG. 8 is a view showing an example in a case where a part of the configuration of the subject observation apparatus according to the first embodiment of the present invention is applied to a capsule medical apparatus. FIG. 9 is a view showing an example when a part of the configuration of the subject observation apparatus according to the first embodiment of the present invention is applied to a rigid endoscope. FIG. 10 is a view showing an example when a part of the configuration of the subject observation apparatus according to the first embodiment of the present invention is combined with a configuration for polarized imaging.

Figure 11:
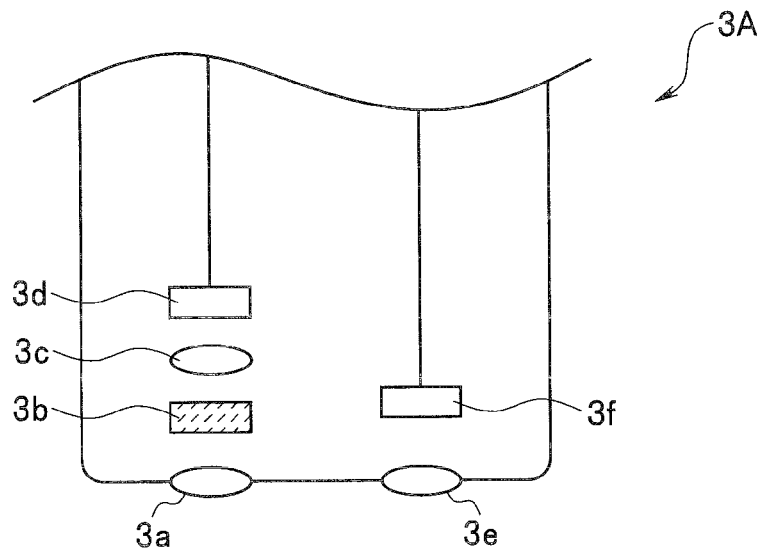
FIG. 11 is a view showing an exemplary configuration of an image pickup section including two image pickup systems, an image pickup system with an optical modulator and an image pickup system without an optical modulator.
Figure 12:
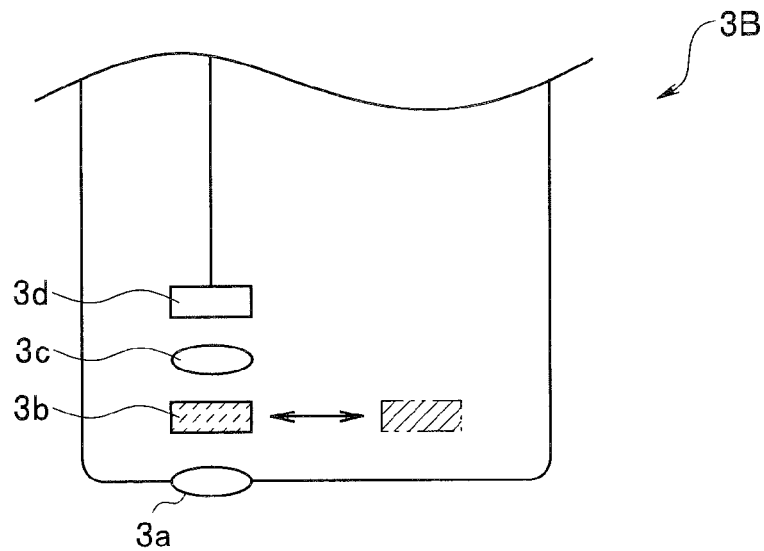
FIG. 12 is a view showing an exemplary configuration of an image pickup section including an optical modulator which is insertable/retractable onto and from an optical path of the light emitted from a first optical system.
Figure 13:
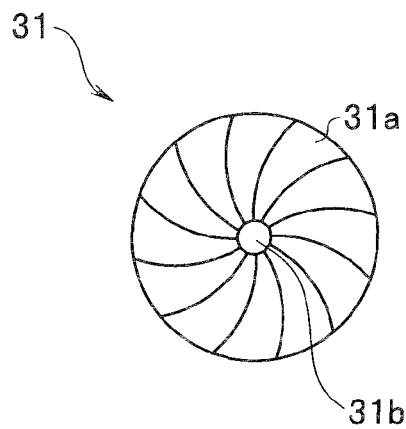
FIG. 13 is a view showing an exemplary configuration in which an area ratio of a light-shielding portion and a light-transmitting portion in the optical modulator can be changed.

FIG. 11 is a view showing an exemplary configuration of an image pickup section including two image pickup systems, an image pickup system with an optical modulator and an image pickup system without an optical modulator. FIG. 12 is a view showing an exemplary configuration of an image pickup section including an optical modulator which is insertable/retractable onto and from an optical path of the light emitted from a first optical system. FIG. 13 is a view showing an exemplary configuration in which an area ratio of a light-shielding portion and a light-transmitting portion in the optical modulator can be changed.

As shown in FIG. 4, the subject observation apparatus 1 includes: an illumination section 2 that emits illumination light to a subject 102A; an image pickup section 3 that generates an image pickup signal by photoelectrically converting the optically modulated return light of the illumination light and outputs the generated image pickup signal; a signal processing section 4 that generates a video signal by signal-processing the image pickup signal and outputs the generated video signal; and a display section 5 that displays an image of the subject 102A based on the video signal.

Note that the subject 102A has at least an inner structure in which the first scattering medium 102b and the second scattering medium 102c are arranged in a random manner.

In addition, in the present embodiment, the illumination light emitted from the illumination section 2 may be either a broadband light or a narrowband light.

As shown in FIG. 5, the image pickup section 3 includes: a first optical system 3a that emits an incident return light as a parallel light having an angle corresponding to an incident angle at which the return light enters the first optical system 3a itself, an optical modulator 3b that optically modulates the parallel light emitted from the first optical system 3a; a second optical system 3c that forms an image of the light modulated by the optical modulator 3b; and an image pickup device 3d that generates an image pickup signal by photoelectrically converting the light whose image has been formed by the second optical system 3c, and outputs the generated image pickup signal.

Note that an optical modulation section in the present embodiment is configured of the first optical system 3a and the optical modulator 3b.

The first optical system 3a and the second optical system 3c are configured of Fresnel lenses having approximately the same diameter.

Note that the first optical system 3a, as long as it can emit the incident return light as a parallel light, is not limited to one configured of a single Fresnel lens, and may be configured by combining a plurality of lenses.

As shown in FIGS. 5 and 6, the optical modulator 3b as the optical modulation section is formed in a disk shape having approximately the same diameter as those of the first optical system 3a and the second optical system 3c, for example. In addition, as shown in FIG. 6, the optical modulator 3b is formed by including a light-shielding portion 3b1, the light transmission rate of which is substantially zero, and a light-transmitting portion 3b2, the light transmission rate of which is substantially 100%.

Note that the optical modulator 3b may be configured of a black plate having a hole as the light-transmitting portion 32b, for example, or may be configured of a liquid crystal shutter capable of changing the light transmission rates (optical characteristics) of the light-shielding portion 3b1 and the light-transmitting portion 3b2.

In addition, the optical modulator 3b is not required to be formed of a specific material, so that the optical modulator 3b may be formed of a glass plate or a metal plate, for example.

Next, the working of the subject observation apparatus 1 of the present embodiment will be described.

Illumination light emitted from the illumination section 2 as a light-emitting section is multiply-scattered in the subject 102A, and thereafter being incident on the first optical system 3a as return lights.

At this time, as shown in FIG. 5, when the forward-scattering direction of the return lights from the surface of the subject 102A is zero degree, the return lights are incident on the first optical system 3a as the lights each having the scattering angle equal to or larger than zero degree and smaller than 90 degrees.

According to the perception obtained by the above-described inference, when the return lights are from the first scattering medium 102b, the return lights have the scattering angle distribution shown by the curve Db in FIG. 3. On the other hand, when the return lights are from the second scattering medium 102c, the return lights have the scattering angle distribution shown by the curve Dc in FIG. 3.

The return lights which are incident on the first optical system 3a are emitted as parallel lights, and thereafter optically modulated by the optical modulator 3b.

At this time, the return lights whose incident angles with respect to the first optical system 3a are equal to or larger than zero degree and equal to or smaller than a predetermined angle $\theta 1$ pass through the light-transmitting portion 3b2 of the optical modulator 3b, so that the lights are emitted to the second optical system 3c with the intensities of the lights substantially maintained. On the other hand, the return lights whose incident angles with respect to the first optical system 3a are larger than the predetermined angle $\theta 1$ and smaller than 90 degrees are shielded by the light-shielding portion 3b1 of the optical modulator 3b.

That is, the optical modulator 3b performs optical modulation on the parallel lights emitted from the first optical system 3a so as to emit the lights to the second optical system 3c with the intensities of the lights substantially maintained when the scattering angles of the return lights are equal to or larger than zero degree and equal to or smaller than the predetermined angle $\theta 1$, and shield the lights when the scattering angles of the return lights are larger than the predetermined angle $\theta 1$ and smaller than 90 degrees. According to this configuration, the scattering angle distributions corresponding to the intensities of the return lights before and after passing through the first optical system 3a and the optical modulator 3b change from the distributions shown by the curves Db and Dc in FIG. 3 to the distributions shown by the curves Dbm and Dcm in FIG. 7.

The parallel lights subjected to the optical modulation by the optical modulator 3b are image-formed by the second optical system 3c, photoelectrically converted by the image pickup device 3d, and thereafter being outputted to the signal processing section 4 as an image pickup signal.

The image pickup signal outputted from the image pickup device 3d as a signal output section is converted into a video signal by the signal processing section 4, and thereafter being outputted on the display section 5. As a result, an image of the subject 102A, in which a difference in the light intensities between the curve Dbm and the curve Dcm in FIG. 7 is exhibited as a difference in brightness, is outputted on the display section 5.

In the present embodiment, as a specific example, it is assumed that the subject 102A is a living tissue, the first scattering medium 102b is a normal tissue, and the second scattering medium 102c is a tumor tissue.

In this case, the second scattering medium 102c has a stronger forward-scattering characteristic than that of the first scattering medium 102b. Accordingly, in the image of the subject 102A outputted on the display section 5, the portion where a tumor tissue exists looks brighter than other portions. That is, when the endoscope and the like provided with the image pickup section 3 having the above-described configuration is used, it is possible to easily identify the region where a tumor tissue showing little characteristic finding exists.

That is, the subject observation apparatus 1 of the present embodiment can identify the region where a desired scattering characteristic is exhibited in the scattering medium including a plurality of regions each having a different scattering characteristic.

According to the subject observation apparatus 1 of the present embodiment, as long as the apparatus is used for the purpose of identifying the region where the second scattering medium 102c exists in the subject 102A which mixedly includes the first scattering medium 102b and the second scattering medium 102c, the apparatus may be used not only for the purpose of discriminating between a normal tissue and a tumor tissue in observation of a living tissue, but also for the purpose of discriminating between a normal portion and abnormal portion in a quality inspection.

Note that the optical modulator 3b according to the present embodiment is not limited to one having the above-described configuration and working. For example, the optical modulator 3b may optically modulate the parallel lights emitted from the first optical system 3a so as to shield the lights when the scattering angles of the return lights are equal to or larger than zero degree and equal to or smaller than the predetermined angle θ1, and emit the lights to the second optical system 3c with the intensities of the lights substantially maintained, when the scattering angles of the return lights are larger than the predetermined angle θ1 and smaller than 90 degrees.

Here, description will be made on an application of the configuration and the like of the subject observation apparatus 1, as a modified example of the present embodiment.

The configuration of the subject observation apparatus 1 of the present embodiment can be applied to a capsule medical apparatus, for example.

A capsule medical apparatus 201 shown in FIG. 8 includes: an exterior member 201a having a light-shielding effect, a cross section of which is U-shaped; and an approximately hemispherically-shaped cover member 201b made of a transparent member, which is water-tightly mounted with adhesive to an opening end of a distal end side of the exterior member 201a.

In a hollow portion inside the exterior member 201a are provided the optical modulator 3b, the second optical system 3c, and the image pickup device 3d. On the other hand, in a hollow portion inside the cover member 201b are provided the first optical system 3a and an LED 202 having a function as a light-emitting section.

Furthermore, the configuration of the subject observation apparatus 1 according to the present embodiment can be applied to a rigid endoscope, for example.

A rigid endoscope 301 shown in FIG. 9 is configured by including an elongated insertion portion 301a and an eyepiece portion 301b.

Inside the insertion portion 301a are arranged in the following order from the distal end side: a first optical system 3a; an optical modulator 3b; a second optical system 3c; and a relay optical system 302.

According to such a configuration of the rigid endoscope 301, the light passed through the second optical system 3c is transmitted by the relay optical system, and thereafter emitted to an eyepiece lens, not shown, provided in the eyepiece portion 301b.

Note that, when observing a subject (scattering medium) using the above-described rigid endoscope 301, an operator may look directly through the eyepiece lens or may connect a camera head at a rear part of the eyepiece lens to view the video outputted on the monitor from the camera head.

Furthermore, the configuration of the subject observation apparatus 1 according to the present embodiment can be used in combination with a configuration for performing polarized imaging, for example.

An image pickup/illumination section 401 shown in FIG. 10 includes: a first optical system 3a; an optical modulator 3b; a second optical system 3c; a light guide 402 that transmits illumination light emitted from a light source, not shown; a polarizing filter 403a that aligns incident lights in a first polarization direction; a polarizing filter 403b that aligns incident lights in a second polarization direction perpendicular to the first polarization direction; and an illumination optical system 404. Note that the second polarization direction is not limited to the direction perpendicular to the first polarization direction, and may be any polarization direction as long as the direction is not parallel with the first polarization direction.

According to such a configuration of the image pickup/illumination section 401, the illumination light emitted from the light source, not shown, is transmitted by the light guide 402 to be aligned in the first polarization direction by the polarization filter 403a, and thereafter emitted, via the illumination optical system 404, to a subject (scattering medium), not shown.

After that, the illumination light emitted to the subject (scattering medium), not shown, is multiply-scattered inside the subject (scattering subject) and then incident on the first optical system 3a as return lights.

The return lights incident on the first optical system 3a are optically modulated by the optical modulator 3b to be aligned in the second polarization direction by the polarization filter 403b, and then image-formed by the second optical system 3c. After that, the image is picked up by the image pickup device 3d.

According to the configuration of the image pickup/illumination section 401, it is possible to acquire an image of the subject (scattering medium) in which the contrast between the region exhibiting a forward-scattering characteristic and the region exhibiting other scattering characteristics in the subject (scattering medium) becomes clearer.

The subject observation apparatus 1 of the present embodiment may further include a configuration in which it is possible to select either one of the state where optical modulation is performed by the optical modulator 3b and the state where the optical modulation is not performed by the optical modulator 3b, when acquiring the image of the subject.

Specifically, such a configuration can be achieved by causing an image pickup section 3A as shown in FIG. 11, for example, to perform a switching operation described below. That is, in the image pickup section 3A which includes: a first image pickup system having a first optical system 3a, an optical modulator 3b, a second optical system 3c and an image pickup device 3d; and a second image pickup system having an objective optical system 3e and an image pickup device 3f, the switching operation is so performed as to output the image pickup signal from only one of the image pickup systems.

Note that the image pickup section capable of selecting the presence and the absence of the optical modulation as described above is not limited to one including two image pickup systems as shown in FIG. 11, but may be one including three image pickup systems, for example.

Furthermore, the configuration in which the presence and the absence of the optical modulation is selectable can be achieved also by causing an image pickup section 3B as shown in FIG. 12, for example, to perform a switching operation described below. That is, in the image pickup section 3B which includes a first optical system 3a, an optical modulator insertable and retractable onto and from the optical path of the light emitted from the first optical system 3a, a second optical system 3c, and an image pickup device 3d, the switching operation is so performed as to change the insertion/retraction state of the optical modulator 3b on the optical path.

The subject observation apparatus 1 of the present embodiment may further include a configuration in which the area ratio of the light-shielding portion 3b1 and the light-transmitting portion 3b2 in the optical modulator 3b is changeable.

Specifically, such a configuration can be achieved as follows. That is, as shown in FIG. 13, for example, in the optical modulator 31 which includes a plurality of plate members 31a, and an opening 31b formed by overlapping the plurality of plate members 31a one another, the size of the opening 31b is changed while moving the plurality of plate members 31a using a mechanism similar to a general diaphragm device.

The light transmission rate of the light-shielding portion 3b1 in the subject observation apparatus 1 according to the present embodiment is not limited to a value around zero, as long as the light transmission rate is relatively lower than that of the light-transmitting portion 3b2. According to such a configuration, by using a plurality of optical modulators 3b which include the light-shielding portions 3b1 each having a different light transmission rate, for example, optical modulation can be performed in stages on the light emitted from the first optical system 3a.

The subject observation apparatus 1 according to the present embodiment may further include a configuration in which necessity and unnecessity of the optical modulation in the optical modulator 3b can be manually switched using a switch and the like. Such a configuration may be achieved by providing a dedicated switching switch, for example, or by switching in conjunction with operations of a magnification lever or a rigidity change lever of the endoscope.

Second Embodiment

Figure 14:
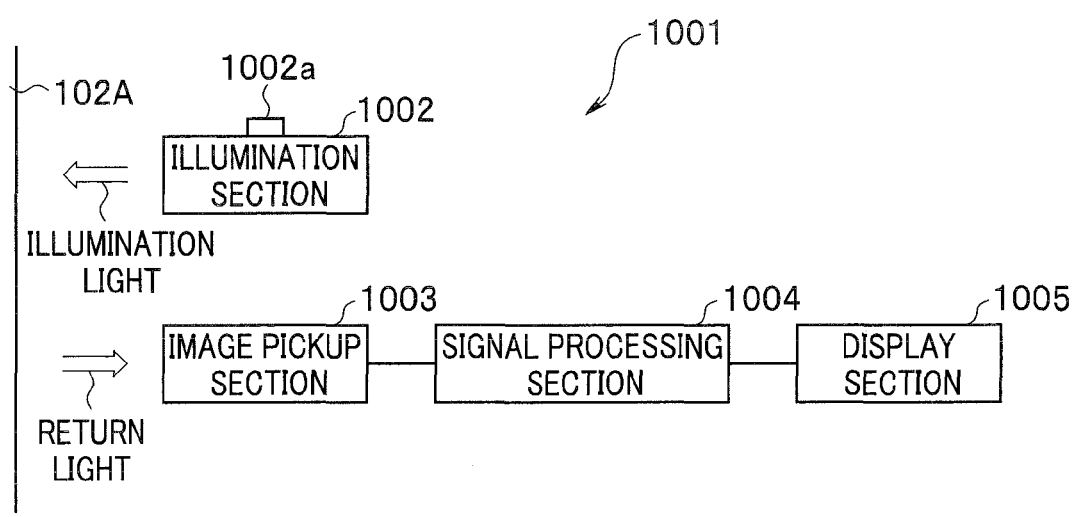
FIG. 14 is a view showing a configuration of a main part of a subject observation apparatus according to a second embodiment of the present invention.
Figure 15:
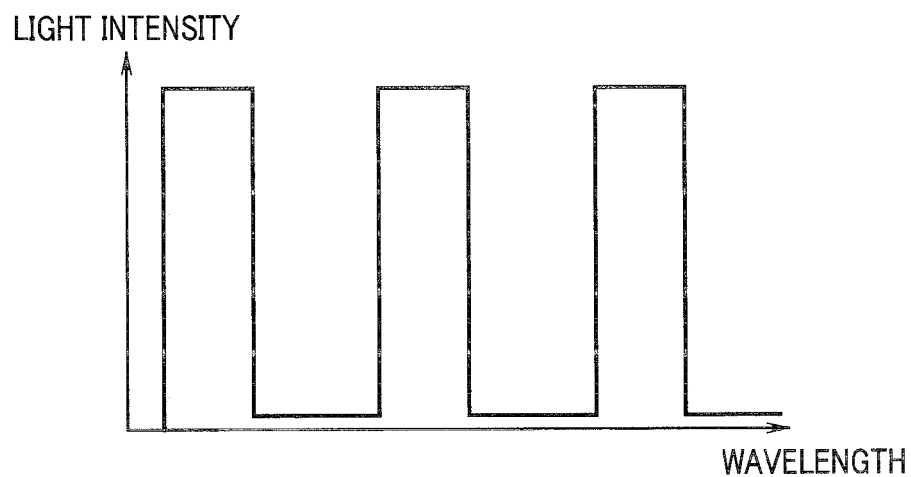
FIG. 15 is a view showing an example of a spectral distribution of a first illumination light emitted from an illumination section included in the subject observation apparatus according to the second embodiment of the present invention.
Figure 16:
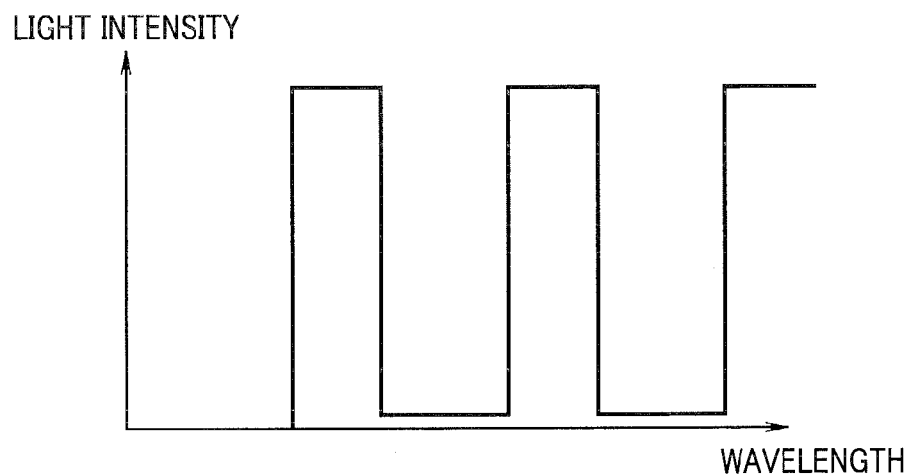
FIG. 16 is a view showing an example of a spectral distribution of a second illumination light emitted from the illumination section included in the subject observation apparatus according to the second embodiment of the present invention.
Figure 17:
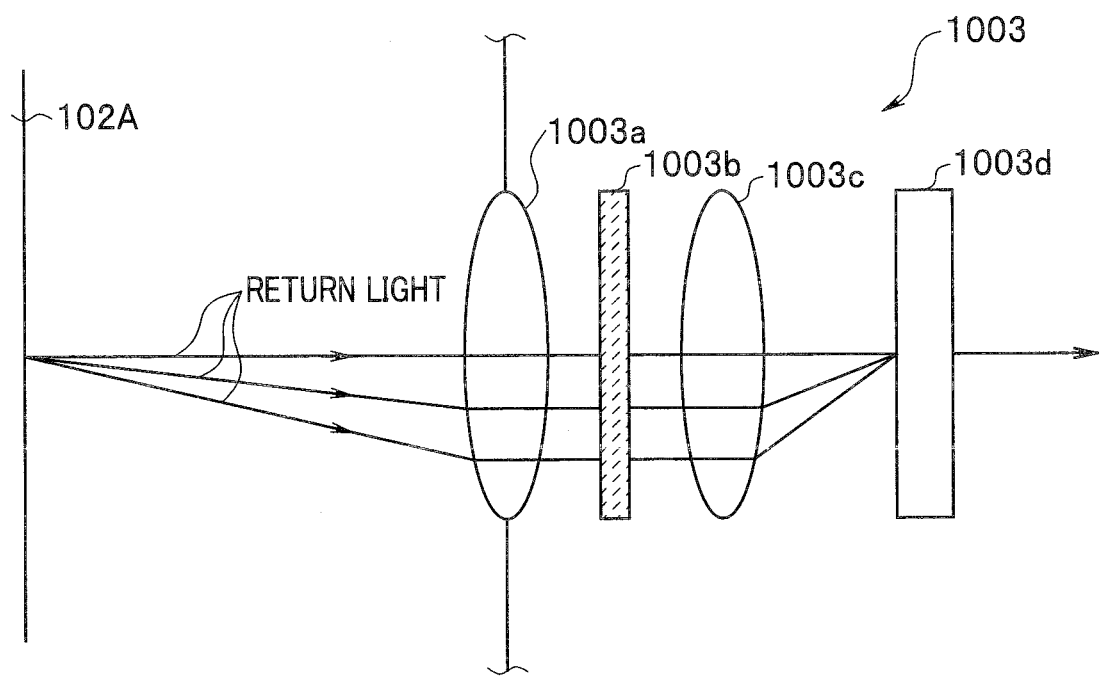
FIG. 17 is a view showing an example of a specific configuration of an image pickup section included in the subject observation apparatus according to the second embodiment of the present invention.
Figure 18:
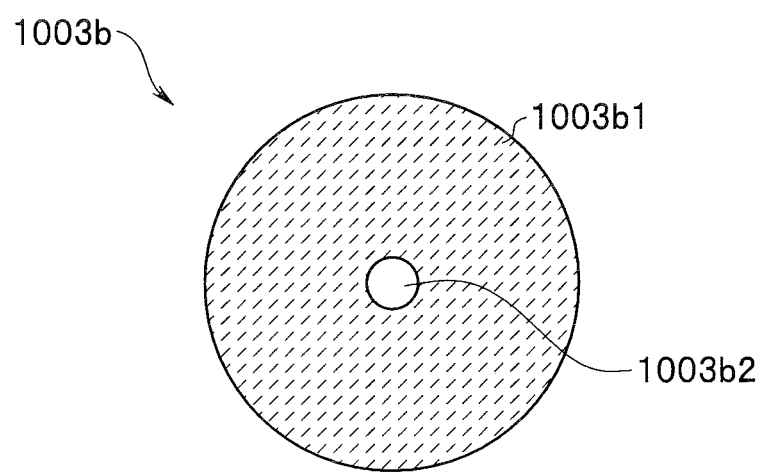
FIG. 18 is a view showing an example of a specific configuration of an optical modulator included in the image pickup section in FIG. 17.
Figure 19:
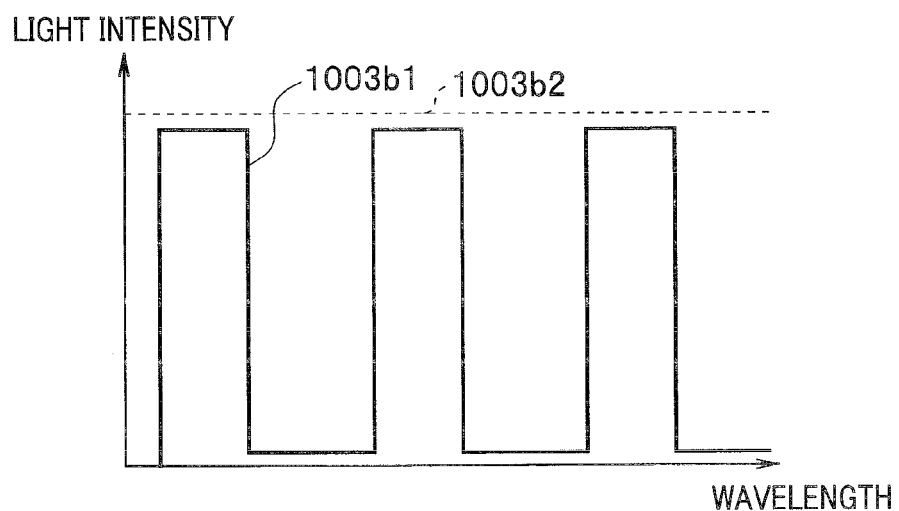
FIG. 19 is a view showing an example of light transmission rates of the light selective-transmitting portion and the light-transmitting portion included in the optical modulator in FIG. 18.
Figure 20:
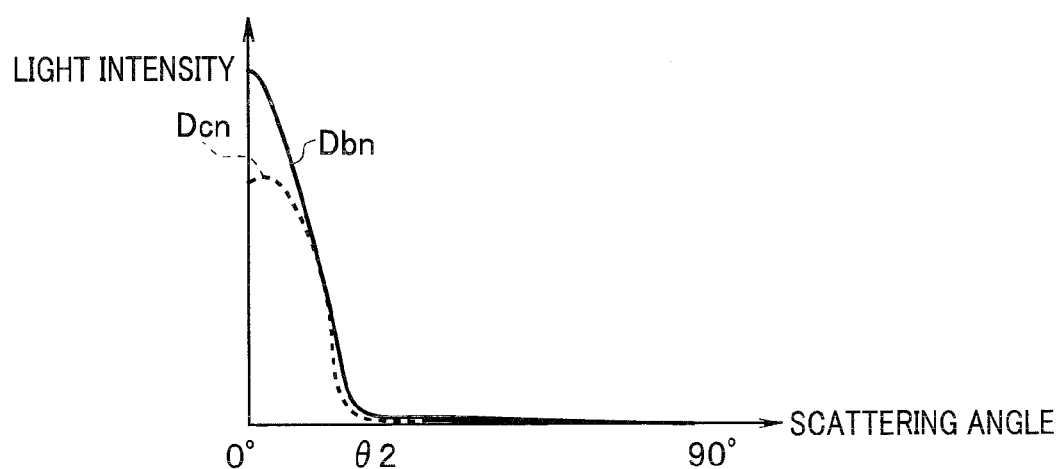
FIG. 20 is a view showing a modulation result in a case where an optical modulation has been performed by the optical modulator in FIG. 18 on the scattering lights having the scattering angle distributions in FIG. 3.

FIGS. 14 to 20 relate to a second embodiment of the present invention. FIG. 14 is a view showing a configuration of a main part of a subject observation apparatus according to the second embodiment of the present invention. FIG. 15 is a view showing an example of a spectral distribution of a first illumination light emitted from an illumination section included in the subject observation apparatus according to the second embodiment of the present invention. FIG. 16 is a view showing an example of a spectral distribution of a second illumination light emitted from the illumination section included in the subject observation apparatus according to the second embodiment of the present invention. FIG. 17 is a view showing an example of a specific configuration of an image pickup section included in the subject observation apparatus according to the second embodiment of the present invention. FIG. 18 is a view showing an example of a specific configuration of an optical modulator included in the image pickup section in FIG. 17. FIG. 19 is a view showing an example of light transmission rates of the light selective-transmitting portion and the light-transmitting portion included in the optical modulator in FIG. 18. FIG. 20 is a view showing a modulation result in a case where an optical modulation has been performed by the optical modulator in FIG. 18 on the scattering lights having the scattering angle distributions in FIG. 3.

As shown in FIG. 14, a subject observation apparatus 1001 includes: an illumination section 1002 that emits illumination light to a subject 102A; an image pickup section 1003 that generates an image pickup signal by photoelectrically converting the optically modulated return light of the illumination light, and outputs the generated image pickup signal; a signal processing section 1004 that generates a video signal by signal-processing the image pickup signal and outputs the generated video signal; and a display section 1005 that displays an image of the subject 102A based on the video signal.

Note that the subject 102A has at least an internal structure in which the above-described first scattering medium 102b and the second scattering medium 102c are arranged in a random manner.

The illumination section 1002 includes a switch 1002a as a spectral characteristic switching section and is capable of emitting an illumination light while switching between two kinds of illumination lights having spectral distributions different from each other. Specifically, the illumination section 1002 is capable of emitting the illumination light while switching between a first illumination light having a first comb-shaped spectral distribution as shown in FIG. 15 and a second illumination light having a second comb-shaped spectral distribution as shown in FIG. 16, for example, using the switch 1002a. Note that the wavelength bands in which the light intensity is maximum do not overlap each other in the first comb-shaped spectral distribution and the second comb-shaped distribution.

As shown in FIG. 17, the image pickup section 1003 is configured by including: a first optical system 1003a that emits an incident return light as a parallel light having an angle corresponding to an incident angle at which the return light enters the first optical system 1003a itself; an optical modulator 1003b that optically modulates the parallel light emitted from the first optical system 1003a; a second optical system 1003c that forms an image of the light modulated by the optical modulator 1003b and an image pickup device 1003d that generates an image pickup signal by photoelectrically converting the light whose image has been formed by the second optical system 1003c.

Note that the optical modulation section of the present embodiment is configured of the first optical system 1003a and the optical modulator 1003b.

The first optical system 1003a and the second optical system 1003c are configured of Fresnel lenses having approximately the same diameter.

Note that the first optical system 1003a, as long as it can emit the incident return light as a parallel light, is not limited to one configured of a single Fresnel lens, and may be configured by combining a plurality of lenses.

As shown in FIGS. 17 and 18, the optical modulator 1003b as an optical modulation section is formed in a disk shape having approximately the same diameter as those of the first optical system 1003a and the second optical system 1003c, for example. In addition, the optical modulator 1003b is formed by including a light selective-transmitting portion 1003b1 and the light-transmitting portion 1003b2 as two regions, the light transmission rates of which are different from each other.

Specifically, as shown in FIG. 19, the light selective-transmitting portion 1003b1 is so formed as to transmit only the lights of wavelength bands coincident with the first comb-shaped spectral distribution and shield the lights of wavelength bands other than the wavelength bands coincident with the first comb-shaped spectral distribution. In addition, the light-transmitting portion 1003b2 is so formed as to transmit substantially all the incident lights, as shown in FIG. 19.

Next, working of the subject observation apparatus 1001 according to the present embodiment will be described.

First, a user operates the switch 1002a to cause the illumination section 1002 to emit the first illumination light.

The first illumination light emitted from the illumination section 1002 as a light-emitting section is multiply-scattered in the subject 102A, and thereafter incident on the first optical system 1003a as return lights.

At this time, as shown in FIG. 17, when the forward-scattering direction of the return lights from the surface of the subject 102A is zero degree, the return lights are incident on the first optical system 1003a as the lights each having the scattering angle equal to or larger than zero degree and smaller than 90 degrees.

According to the perception obtained from the above-described inference, if the return lights are from the first scattering medium 102b, the return lights have the scattering angle distribution shown by the curve Db in FIG. 3. On the other hand, the return lights are from the second scattering medium 102c, the return lights have the scattering angle distribution shown by the curve Dc in FIG. 3.

The return lights of the first illumination light pass through the first optical system 1003a, and thereafter incident, as parallel lights, on the optical modulator 1003b.

Since the light selective-transmitting portion 1003b1 has such a characteristic as to transmit only the lights of the wavelength bands coincident with the first comb-shaped spectral distribution, the parallel lights as the return lights of the first illumination light pass through the optical modulator 1003b.

That is, the optical modulator 1003b having the above-described configuration transmits the parallel lights corresponding to the return lights of the first illumination light with the intensities thereof substantially maintained, without performing optical modulation on the return lights.

After that, the parallel lights which have passed through the optical modulator 1003b are image-formed by the second optical system 1003c, and then photoelectrically converted by the image pickup device 1003d to be outputted as an image pickup signal to a signal processing section 1004.

The image pickup signal outputted from the image pickup device 1003d as a signal output section is converted into a video signal by the signal processing section 1004, and thereafter outputted on the display section 1005. As a result, the image of the subject 102A having almost natural color is outputted on the display section 1005.

Next, the user operates the switch 1002a to cause the illumination section 1002 to emit the second illumination light.

The second illumination light emitted from the illumination section 1002 as a light-emitting section is multiply-scattered in the subject 102A, and thereafter being incident on the first optical system 1003a as return lights.

At this time, as shown in FIG. 17, when the forward-scattering direction of the return lights from the surface of the subject 102A is zero degree, the return lights are incident on the first optical system 1003a as the lights each having the scattering angle equal to or larger than zero degree and smaller than 90 degrees.

According to the perception obtained by the above-described inference, when the return lights are from the first scattering medium 102b, the return lights have the scattering angle distribution shown by the curve Db in FIG. 3. On the other hand, when the return lights are from the second scattering medium 102c, the return lights have the scattering angle distribution shown by the curve Dc in FIG. 3.

The return lights of the second illumination light pass through the first optical system 1003a, and thereafter are incident, as parallel lights, on the optical modulator 1003b.

At this time, the return lights whose incident angles with respect to the first optical system 1003a are equal to or larger than zero degree and equal to or smaller than a predetermined angle $\theta 2$ pass through the light-transmitting portion 1003b2 of the optical modulator 1003b, so that the lights are emitted to the second optical system 1003c with the intensities of the lights being substantially maintained. On the other hand, the return lights whose incident angles with respect to the first optical system 1003a are larger than the predetermined angle $\theta 2$ and smaller than 90 degrees are shielded by the light selective-transmitting portion 1003b1 of the optical modulator 1003b.

That is, the optical modulator 1003b having the above-described configuration optically modulates the parallel lights corresponding to the return lights of the second illumination light so as to emit the lights to the second optical system 1003c with the intensities of the lights substantially maintained when the scattering angles of the return lights are equal to or larger than zero degree and equal to or smaller than a predetermined angle $\theta 2$, and shield the lights when the scattering angles of the returns lights are larger than the predetermined angle $\theta 2$ and smaller than 90 degrees. Accordingly, the scattering angle distributions corresponding to the intensities of the return lights of the second illumination light before and after passing through the first optical system 1003a and the optical modulator 1003b change from the distributions shown by the curves Db and Dc in FIG. 3 to the distributions shown by the curves Dbn and Dcn in FIG. 20.

The parallel lights which have been optically modulated by the optical modulator 1003b are image-formed by the second optical system 1003c, photoelectrically converted by the image pickup device 1003d, and thereafter outputted to the signal processing section 1004 as an image pickup signal.

The image pickup signal outputted from the image pickup device 1003d as a signal output section is converted into a video signal by the signal processing section 1004, and thereafter being outputted on the display section 1005. As a result, on the display section 1005 is displayed the image of the subject 102A having almost natural color in which the light intensity difference between the curve Dbn and the curve Dcn in FIG. 20 is exhibited as a brightness difference.

In the present embodiment, as a specific example, it is assumed that the subject 102A is a living tissue, the first scattering medium 102b is a normal tissue, and the second scattering medium 102c is a tumor tissue.

In this case, since the second scattering medium 102c has a stronger forward-scattering characteristic than that of the first scattering medium 102b, the portion where the tumor tissue exists looks brighter than other portions in the image of subject 102A displayed on the display section 1005. That is, when endoscopes and the like provided with the image pickup section 1003 having the above-described configuration are used, it is possible to easily identify the region where the tumor tissue which shows little characteristic finding.

Furthermore, with the subject observation apparatus 1001 of the present embodiment, the switching between whether or not to perform optical modulation in the optical modulator 1003b can be performed only by switching the kinds of the illumination lights emitted from the illumination section 1002, without changing the characteristic of the optical modulator 1003b itself.

That is, the subject observation apparatus 1001 of the present embodiment can identify the region exhibiting a desired scattering characteristic in the scattering medium which has a plurality of regions each having a different scattering characteristic, with a simple operation.

Now, as a modified example of the present embodiment, an application example of the configuration of the subject observation apparatus 1001 will be described.

With the configuration of the subject observation apparatus 1001 of the present embodiment, the color of the image of the subject 102A may be changed when the optical modulation is performed in the optical modulator 1003b.

Specifically, in the second comb-shaped spectral distribution shown in FIG. 16, the number of the wavelength bands (the number of the comb teeth in the second comb-shaped spectral distribution) in which the light intensity becomes maximum is increased or decreased in accordance with the characteristic of the light selective-transmitting portion 1003b1, or the maximum value of the light intensity (the height of the comb teeth in the second comb-shaped spectral distribution) is made smaller than that in the first comb-shaped spectral distribution as shown in FIG. 15.

With the above-described configuration, it is possible to make the color of the image different in a visible range depending on the presence and absence of the optical modulation in the optical modulator 1003b. In addition, with the above-described configuration, it is also possible to make the color of image different in an infrared range and the visible range depending on the presence and absence of the optical modulation in the optical modulator 1003b.

The illumination section 1002 in the subject observation apparatus 1001 of the present embodiment is not limited to the illumination section which emits an illumination light while switching between the first illumination light without the optical modulation in the optical modulator 1003b and the second illumination light with the optical modulation in the optical modulator.

Specifically, for example, the illumination section 1002 may be configured to be able to gradually change the spectral distribution of the illumination light emitted by the illumination section itself, from the first comb-shaped spectral distribution to the second comb-shaped spectral distribution (and vice versa). Such a configuration makes it possible for the optical modulator 1003b to continuously or gradually perform the optical modulation on the light emitted from the first optical system 1003a.

In the configuration of the subject observation apparatus 1001 of the present embodiment, the switching of the illumination lights emitted from the illumination section 1002 is not limited to the switching performed through the switch 1002a. For example, the switching may be performed in conjunction with operation of the magnification lever or the rigidity change lever in the endoscope.

Note that the present invention is not limited to the above-described embodiments, and various modifications can be made without departing from the gist of the present invention.

What is claimed is:

1. A subject observation apparatus comprising:
    a light-emitting section for emitting a light to a subject;
    a spectral distribution switching section for switching the light emitted from the light-emitted section to either a first light having a first spectral distribution or a second light having a second spectral distribution different from the first spectral distribution;
    an optical modulation section for detecting a scattering angle of a return light from the subject and performing optical modulation on the return light in accordance with the scattering angle, when the first light or the second light switched by the spectral distribution switching section is emitted to the subject; and
    a signal output section for generating a signal to show a state of light scattering in the subject based on the light subjected to the optical modulation by the optical modulation section, and outputting the generated signal,
    wherein the optical modulation section is configured as a plate-shaped optical element which includes at a center portion thereof a light-transmitting portion for transmitting a light when the scattering angle is equal to or larger than zero degree and equal to or smaller than a predetermined angle in a case where a forward-scattering direction of the return light is zero degree, and includes a light selective-transmitting portion around the light transmitting portion, the light selective-transmitting portion transmitting only lights of wavelength bands coincident with the first spectral distribution and shielding lights of wavelength bands other than the wavelength bands coincident with the first spectral distribution, when the scattering angle is larger than the predetermined angle and smaller than 90 degrees.

2. The subject observation apparatus according to claim 1, wherein the signal output section is an image pickup device for generating an image pickup signal by photoelectrically converting the light subjected to the optical modulation by the optical modulation section and outputting the generated image pickup signal.

3. The subject observation apparatus according to claim 1, wherein the subject is a scattering medium including a plurality of regions each having a different light scattering characteristic.

4. The subject observation apparatus according to claim 1, wherein wavelength bands of a maximum light intensity of the first spectral distribution do not overlap with wavelength bands of a maximum light intensity of the second spectral distribution.

5. The subject observation apparatus according to claim 4, wherein the first spectral distribution and the second spectral distribution have comb shapes, and wavelength bands of the parts corresponding to the comb shapes do not overlap each other.

* * * * *